United States Patent
Enomoto et al.

(10) Patent No.: US 9,952,508 B2
(45) Date of Patent: Apr. 24, 2018

(54) COMPOUNDERS FOR ENHANCING GENERATION OF CHEMICAL SPECIES

(71) Applicant: TOYO GOSEI CO., LTD., Ichikawa-shi, Chiba (JP)

(72) Inventors: Satoshi Enomoto, Chiba (JP); Yusuke Suga, Chiba (JP)

(73) Assignee: Toyo Gosei Co., Ltd., Ichikawa-Shi, Chiba (JP)

( * ) Notice: Subject to any disclaimer, the term of this patent is extended or adjusted under 35 U.S.C. 154(b) by 0 days.

(21) Appl. No.: 15/025,518

(22) PCT Filed: Sep. 30, 2014

(86) PCT No.: PCT/JP2014/005008
§ 371 (c)(1),
(2) Date: Mar. 28, 2016

(87) PCT Pub. No.: WO2015/045426
PCT Pub. Date: Apr. 2, 2015

(65) Prior Publication Data
US 2016/0225611 A1    Aug. 4, 2016

Related U.S. Application Data

(60) Provisional application No. 61/960,923, filed on Sep. 30, 2013.

(51) Int. Cl.
G03F 7/004 (2006.01)
G03F 7/038 (2006.01)
(Continued)

(52) U.S. Cl.
CPC ............ *G03F 7/0382* (2013.01); *C07C 59/64* (2013.01); *C07C 217/18* (2013.01);
(Continued)

(58) Field of Classification Search
CPC ........ G03F 7/004; G03F 7/0045; G03F 7/038; G03F 7/0382; G03F 7/0392; C08F 220/30; C07C 59/64; C07C 217/18
(Continued)

(56) References Cited

U.S. PATENT DOCUMENTS 4,897,223 A    1/1990  Eckstein et al.
6,011,178 A *  1/2000  Werbitzky .............. C07C 45/46
                                                    564/321
(Continued)

FOREIGN PATENT DOCUMENTS

EP    1023835 A1 *  8/2000  ............. A01N 35/04
JP    58216139 A    12/1983
(Continued)

OTHER PUBLICATIONS

Pastor-Perez et al, A Tetramethoxybenzophenone as Efficient Triplet Photocatalyst for the Transformation of Diazo Compounds, Journal of Organic Chemistry, 72, 1541-1544 (2007).*
(Continued)

*Primary Examiner* — Amanda C Walke
(74) *Attorney, Agent, or Firm* — TraskBritt, P.C.

(57) ABSTRACT

A reagent that enhances acid generation of a photoacid generator and composition containing such reagent is disclosed.

14 Claims, 5 Drawing Sheets

(51) Int. Cl.

| | | |
|---|---|---|
| *C07C 217/18* | (2006.01) | |
| *C08F 220/30* | (2006.01) | |
| *C07C 59/64* | (2006.01) | |
| *H01L 21/02* | (2006.01) | |
| *H01L 21/311* | (2006.01) | |
| *H01L 21/027* | (2006.01) | |
| *G03F 7/039* | (2006.01) | |
| *G02F 1/1333* | (2006.01) | |

(52) U.S. Cl.
CPC .......... *C08F 220/30* (2013.01); *G03F 7/0045* (2013.01); *G03F 7/038* (2013.01); *G03F 7/0392* (2013.01); *G03F 7/0397* (2013.01); *H01L 21/0274* (2013.01); *H01L 21/0277* (2013.01); *H01L 21/0279* (2013.01); *H01L 21/02118* (2013.01); *H01L 21/311* (2013.01); *H01L 21/31111* (2013.01); *G02F 1/133345* (2013.01)

(58) Field of Classification Search
USPC ..... 568/332, 308, 640; 430/270.1, 322, 325, 430/329, 330, 923; 526/213, 299
See application file for complete search history.

(56) References Cited

U.S. PATENT DOCUMENTS

| | | | | |
|---|---|---|---|---|
| 6,060,170 | A * | 5/2000 | Burgoyne, Jr. | ........ C08G 65/40 257/E23.077 |
| 7,851,252 | B2 | 12/2010 | Nealey et al. | |
| 9,423,690 | B2 * | 8/2016 | Takizawa | ............. C08F 14/185 |
| 2006/0217453 | A1 * | 9/2006 | Lauer | .................... B82Y 30/00 522/35 |
| 2009/0275720 | A1 * | 11/2009 | Hunt | ..................... C08F 220/30 526/320 |
| 2013/0105297 | A1 * | 5/2013 | Johnstone | ................. C08F 2/50 204/157.93 |
| 2015/0140493 | A1 * | 5/2015 | Enomoto | ............. C07D 317/22 430/322 |
| 2015/0376438 | A1 * | 12/2015 | Enomoto | .............. H01L 21/311 522/154 |

FOREIGN PATENT DOCUMENTS

| | | |
|---|---|---|
| JP | 60016948 A | 1/1985 |
| JP | 63230772 A | 9/1988 |
| JP | 09241270 A | 9/1997 |
| JP | 11269107 | 10/1999 |
| JP | 11322900 | 11/1999 |
| JP | 2000239648 | 9/2000 |
| JP | 2004361636 A | 12/2004 |
| JP | 2010059067 | 3/2010 |
| JP | 2013517345 | 5/2013 |
| WO | 2012050147 A1 | 4/2012 |
| WO | 2015045426 A1 | 4/2015 |

OTHER PUBLICATIONS

Machine translation of JP 2013-080004 (no date).*
PCT International Search Report, PCT/JP2014/005008 dated Jan. 6, 2015.
PCT International Written Opinion, PCT/JP2014/005008 dated Jan. 6, 2015.
Japanese Office Action for copending application No. 2016-511464 dated Feb. 7, 2018 with English translation.

* cited by examiner

In a solution

In a film

COMPOUNDERS FOR ENHANCING GENERATION OF CHEMICAL SPECIES

CROSS-REFERENCE TO RELATED APPLICATIONS

This application is a national phase entry under 35 U.S.C. § 371 of International Patent Application PCT/JP2014/005008, filed Sep. 30, 2014, designating the United States of America and published in English as International Patent Publication WO 2015/045426 A1 on Apr. 2, 2015, which claims the benefit under Article 8 of the Patent Cooperation Treaty to United States and 35 U.S.C. § 119 of Provisional Patent Application Ser. No. 61/960,923, filed Sep. 30, 2013.

TECHNICAL FIELD

Several aspects of this application relate to the fields of compounders (compounds) that enhance a generation of a chemical species such as acid and base. Typical examples of compounders relating to an aspect of this disclosure can be used as constituent of photoresist compositions that can be applied to fabrication of interlayer insulating films of devices such as a liquid crystal display (LCD), an organic electroluminescent display (OLED) and a semiconductor device. More typical examples of such compounders relating to an aspect of this disclosure are those that can be excited by absorbing a light, the wavelength of which is in a range from 200 nm to 400 nm and donates energy or an electron to a photoacid generator (PAG) contained in photoresist so that the PAG generates acid.

BACKGROUND

Current high-resolution lithographic processes are based on chemically amplified resists (CARs) and are used to pattern features with dimensions less than 100 nm.

A method for forming pattern features with dimensions less than 100 nm is disclosed in U.S. Pat. No. 7,851,252 (filed on Feb. 17, 2009), the disclosure of which is hereby incorporated herein in its entirety by this reference.

BRIEF SUMMARY

A compounder that assists generation of a chemical species such as an acid and a composition are disclosed herein. Typically, such compounder assists the generation of Brönsted acid or Brönsted base from a precursor. Furthermore, such a compounder can be utilized to enhance the generation of a Lewis acid or Lewis base. Typically, such a compounder in its ground state or excited state donates energy or an electron to a precursor or accepts energy or an electron from a precursor to form a reactive intermediate or an excited state of the precursor that can easily generate a chemical species. Such a compounder can exist in unchanged form until such compounder interacts or reacts with the precursor. Alternatively, such a compounder can be generated from a reagent in situ before such compounder interacts or reacts with the precursor. In that case, such compounder can be generated in situ by a reaction of such reagent or an intermediate generated from such reagent with a chemical species. Alternatively, such a compounder can be generated by a unimolecular reaction of such reagent. It is preferred that such compounder exhibits longer cutoff wavelength in its absorption spectrum than such reagent.

A compounder related to an aspect of this disclosure has the following characteristics: the compounder absorbs a light, the wavelength of which is longer than 220 nm; and the compounder is capable of sensitizing a precursor to generate a chemical species from the precursor.

Typical examples of such chemical species are an acid and a base. More typical examples of such chemical species are Brönsted acids and Brönsted bases. Furthermore, such a compounder has a characteristic that a molar absorption coefficient of the compounder at 400 nm, when measured in a solution, is equal to or lower than 200. It is preferred that the molar absorption coefficient of such compounder at 400 nm, when measured in a solution, is equal to or lower than 100. It is more preferable that the molar absorption coefficient of such compounder at 400 nm, when measured in a solution, is equal to or lower than 50.

Typically, such a compounder has a characteristic that a ratio of an absorbance at 365 nm ("$Ab_{365}$") to an absorbance at 400 nm ("$Ab_{400}$"), when measured in a solution, is equal to or greater than 20.

It is preferred that a ratio of an absorbance at 365 nm ("$Ab_{365}$") to an absorbance at 400 nm ("$Ab_{400}$") of such compounder, when measured in a solution, is equal to or greater than 50.

It is more preferable that such a ratio of an absorbance at 365 nm ("$Ab_{365}$") to an absorbance at 400 nm ("$Ab_{400}$") of such compounder, when measured in a film, is equal to or greater than 100.

A reagent relating to an aspect of this disclosure is capable of generating the compounder mentioned above. Typically, supply of energy to a film containing such reagent generates the compounder from the reagent. The compounder has a longer conjugation length than the reagent.

A reagent relating to an aspect of this disclosure has at least two pi-electron systems. A compounder having at least two pi-electron systems is generated from such a reagent. An electronic interaction between the at least two pi-electron systems in such a compounder is stronger than an electronic interaction between the at least two pi-electron systems in the reagent. Such a reagent generates the compounder through processes triggered by supplying energy to the film.

Typical examples for such a compounder are diaryl ketones such as alkoxy (or aryloxy) benzophenone, arylalkyl ketones and carbazoles. For example, a composition relating to an aspect of this disclosure contains at least one of such compounder and reagent that is to form such compounder, a precursor that is to form a chemical species, and a compound that is to react with the chemical species. Such a composition can be applied as a photoresist to fabrication of a device such as semiconductor device and electro-optical device. A typical example of such precursor is a photoacid generator (PAG), while a typical example of such compound is a polymer containing a substituent that is acid-dissociable, such as an ester group. Typically, a set of processes for fabricating devices includes a step in which the composition is applied to a member to form a coating film and a step in which the coating film is exposed to a light, the wavelength of which is longer than 200 nm.

In the case where such a compounder is used as a constituent of a photoresist composition that can be applied to interlayer insulating films of display devices such as an LCD and an OLED, it is preferred that the compounder has a very low absorption coefficient at wavelengths longer than or equal to 400 nm since the interlayer insulating films of such display device transmits visible lights or lights having wavelengths longer than 400 nm. It is more preferred that such a compounder exhibit little absorption at wavelengths longer than 400 nm.

A composition relating to an aspect of this disclosure contains a precursor that is to generate a chemical species and at least one of the compounder and the reagent mentioned above. Typical examples of such a reagent have a shorter cutoff wavelength than a compounder formed from such a reagent. Even if a coating film formed by such composition is thick, a light penetrates deeply into the coating film and such a compounder can be generated even in the depths of the coating film.

Typically, such a precursor is a PAG. The composition can further contain a compound capable of reacting with the chemical species. Such a composition can be used as a photoresist for formation of an interlayer insulating film of a device or constituent material for at least one portion of an interlayer insulating film of a device.

A polymer relating to an aspect of this disclosure includes a first moiety capable of acting as a photosensitizing moiety and a second moiety that is to react with a chemical species. Such a polymer may further include a third moiety that is to generate the chemical species.

A method for manufacturing a device relating to an aspect of this disclosure is carried out by using any one of such compositions or such polymers mentioned above. Such a composition may contain at least one of such compounder mentioned above and such reagent.

A method for manufacturing a device relating to an aspect of this disclosure includes the following steps: first, application of a solution of any one of the compositions mentioned above to a member, such that a coating film including such composition is formed on the member; second, irradiation of the coating film with at least one of an electromagnetic ray and a particle ray such that a first portion of the coating film is exposed to the at least one of the electromagnetic ray and the particle ray, while a second portion of the coating film is not exposed to the at least one of the electromagnetic ray and the particle ray; and third, removal of the first portion.

Such a method can further include a step of etching of the member such that a third portion of the member on which the first portion has been present is etched.

In such a method, a contact hole can be formed by the removal of the first portion. Such a method can further include a step of formation of an active layer. The active layer can be connected to an electrode, such as a pixel electrode, by disposing a conductive material at least in the contact hole.

In such method, a light of a wavelength ranging from 350 nm to 400 nm can be used as the electromagnetic ray used for such method.

BRIEF DESCRIPTION OF THE DRAWINGS

In the drawings, which illustrate what is currently considered to be the best mode for carrying out several aspects of this disclosure.

DETAILED DESCRIPTION

Experimental Procedures

Synthesis of 2,2',4,4'-tetramethoxybenzophenone (Compounder A)

Figure 1:
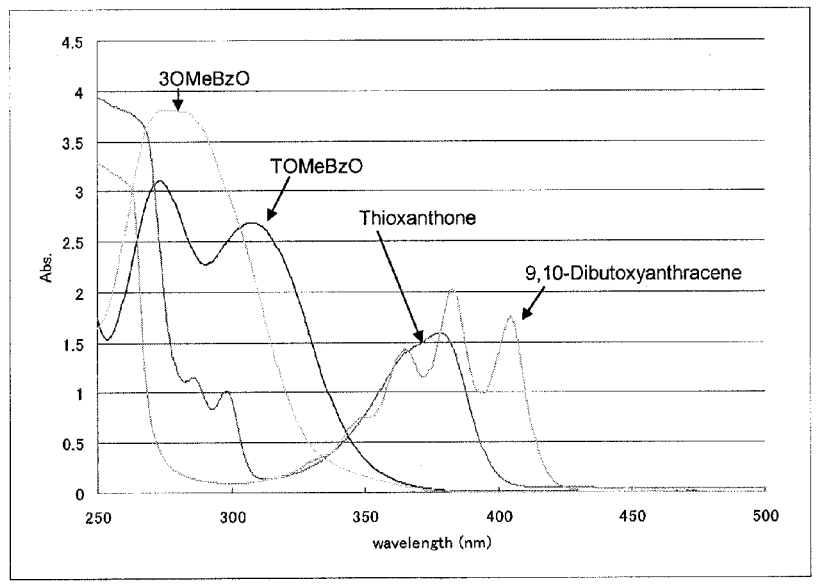
FIG. 1 shows absorption spectra of compounders relating to an aspect of this disclosure.
Figure 1:
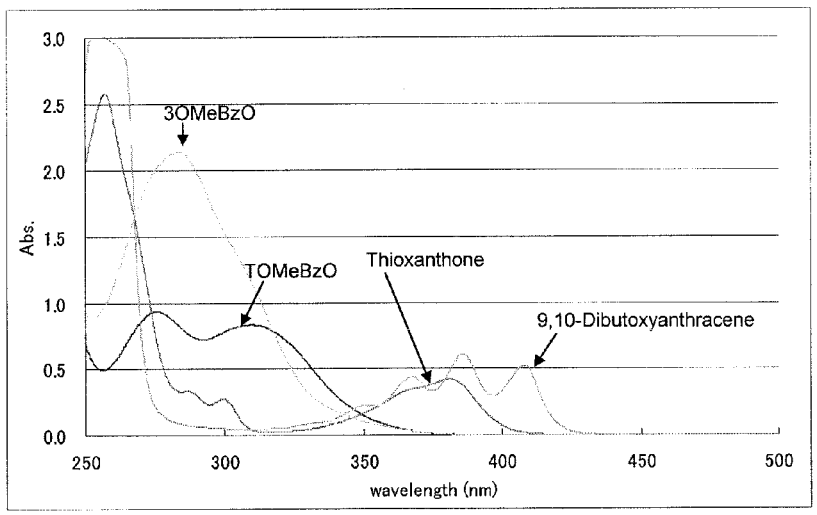

2.00 g of 2,2',4,4'-tetrahydroxybenzophenone 3.68 g of dimethyl sulfate and 4.03 g of potassium carbonate are dissolved in 12.0 g of acetone. The mixture is stirred at reflux temperature for 8 hours. Next, the mixture is cooled to 25 degrees Celsius and is further stirred for 10 minutes after addition of 60.0 g of water and a deposit is filtrated. Then, the deposit is dissolved in 20.0 g ethyl acetate and the organic phase is washed with water. Thereafter, the ethyl acetate is distilled away, and the resultant is purified by recrystallization using 15.0 g of ethanol, thereby obtaining 1.40 g of 2,2',4,4'-tetramethoxybenzophenone.

Chem. 1

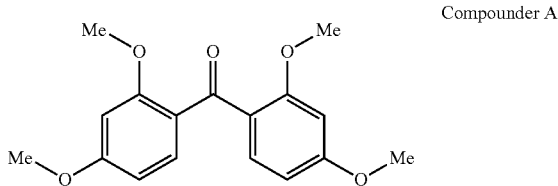

Compounder A

Synthesis of bis-(2,4-dimethoxyphenyl)-dimethoxymethane 7.0 g of 2,2',4,4'-tetramethoxybenzophenone is dissolved in 27.8 g of thionyl chloride. The mixture is stirred at reflux temperature for 5 hours. Next, thionyl chloride is distilled away and the resultant is dissolved in 15 g of toluene. Then, the prepared solution is added dropwise over 1 hour to 30.1 g of methanol solution containing 5.0 g of sodium methoxide at 5 degrees Celsius. Once the addition has been completed, the mixture is warmed up to 25 degrees Celsius while stirring for 2 hours. Then, the mixture is further stirred after an addition of 50 g of pure water. Next, the methanol is distilled away, the resultant is extracted by 35 g of toluene, and the organic phase is washed with water. Thereafter, toluene is distilled away, thereby obtaining 3.87 g of crude bis-(2,4-dimethoxyphenyl)-dimethoxymethane as an oil.

Synthesis of 2,2-bis-(2,4-dimethoxyphenyl)-1,3-dioxolane (Reagent A)

3.8 g of crude bis-(2,4-dimethoxyphenyl)-dimethoxymethane, 0.03 g of compher sulfonic acid and 2.03 g of ethyleneglycol are dissolved in 5.7 g of tetrahydrofran. The mixture is stirred at 25 degrees Celsius for 72 hours. Next, the organic solvents are distilled away and the resultant is dissolved in 11 g of dichloromethane. Thereafter, the mixture is further stirred after addition of 5% aqueous solution of sodium carbonate and the organic phase is washed with 5% aqueous solution of sodium carbonate and water. Thereafter, dichloromethane is distilled away, and the residue is purified by silica gel column chromatography (ethyl acetate:hexane:triethylamine=10:90:0.01), thereby obtaining 2.5 g of 2,2-bis-(2,4-dimethoxyphenyl)-1,3-dioxolane (Reagent A).

Chem. 2

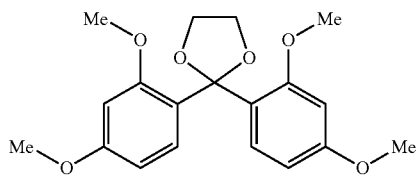

Reagent A

Synthesis of
2,4-dimethoxy-4'-methoxy-benzophenone
(Compounder B)

Synthesis of 2,4-dimethoxy-4'-methoxy-benzophenone as a target substance is synthesized and obtained according to the synthesis of Compounder A mentioned above, except for using 2,4-dimethoxy-4'-hydroxybenzophenone instead of 2,2',4,4'-tetrahydroxybenzophenone for the synthesis of Compounder A.

Chem. 3

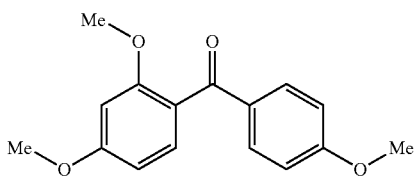

Compounder B

Synthesis of 2,4-dimethoxy-4'-(2-vinyloxy-ethoxy)-benzophenone 2.00 g of 2,4-dimethoxy-4'-hydroxybenzophenone, 2.48 g of 2-chloroethyl vinyl ether and 3.21 g of potassium carbonate are dissolved in 12.0 g of dimethyl formamide. The mixture is stirred at 110 degrees Celsius for 15 hours. Next, the mixture is cooled to 25 degrees Celsius and is further stirred after addition of 60.0 g of water, then extracted with 24.0 g toluene and the organic phase is washed with water. Thereafter, toluene is distilled away, thereby obtaining 3.59 g of 2,4-dimethoxy-4'-(2-vinyloxy-ethoxy)-benzophenone.

Synthesis of 2,4-dimethoxy-4'-(2-hydroxy-ethoxy)-benzophenone 3.59 g of 2,4-dimethoxy-4'-(2-vinyloxy-ethoxy)-benzophenone, 0.28 g of pyridinium p-toluenesulfonate and 2.1 g of water are dissolved in 18.0 g of acetone. The mixture is stirred at 35 degrees Celsius for 12 hours. Next, the mixture is further stirred after addition of 3% aqueous solution of sodium carbonate, then extracted with 28.0 g ethyl acetate and the organic phase is washed with water. Thereafter, ethyl acetate is distilled away, thereby obtaining 3.04 g of 2,4-dimethoxy-4'-(2-hydroxy-ethoxy)-benzophenone.

Synthesis of 2,4-dimethoxy-4'-(2-methacryloxy-ethyl)-benzophenone (Compounder C)

3.0 g of 2,4-dimethoxy-4'-(2-hydroxy-ethoxy)-benzophenone and 1.7 g of methacrylic anhydride are dissolved in 21 g of tetrahydrofuran. 1.2 g of triethylamine dissolved in 3.6 g of tetrahydrofuran is added dropwise to the tetrahydrofuran solution containing 2,4-dimethoxy-4'-(2-hydroxy-ethoxy)-benzophenone over 10 minutes. Next, the mixture is stirred at 25 degrees Celsius for 3 hours. Thereafter, the mixture is further stirred after addition of water, then extracted with 30 g ethyl acetate and the organic phase is washed with water. Thereafter, ethyl acetate is distilled away, and the residue is purified by silica gel column chromatography (ethyl acetate:hexane=1:9), thereby obtaining 2.72 g of 2,4-dimethoxy-4'-(2-methacryloxy-ethyl)-benzophenone.

Chem. 4

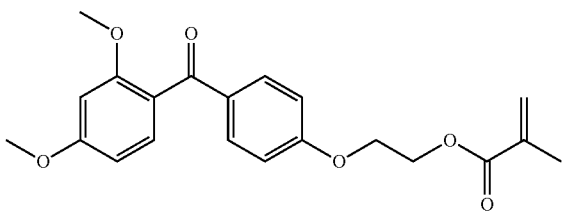

Compounder C

Synthesis of 2,4-dimethoxy-4'-(2-acetoxy-ethoxy)-benzophenone

Synthesis of 2,4-dimethoxy-4'-(2-acetoxy-ethoxy)-benzophenone as a target substance is synthesized and obtained according to the synthesis of Compounder C mentioned above, except for using acetic anhydride instead of methacrylic anhydride for the synthesis of Compounder C.

Synthesis of (2,4-dimethoxyphenyl)-[4'-(2-hydroxy-ethoxy)-phenyl]-dimethoxymethane Synthesis of (2,4-dimethoxyphenyl)-[4'-(2-hydroxy-ethoxy)-phenyl]-dimethoxymethane as a target substance is synthesized and obtained according to the synthesis of bis-(2,4-dimethoxyphenyl)-dimethoxymethane mentioned above, except for using 2,4-dimethoxy-4'-(2-acetoxy-ethyl)-benzophenone instead of 2,2',4,4'-tetramethoxybenzophenone for the synthesis of bis-(2,4-dimethoxyphenyl)-dimethoxymethane.

Synthesis of 2-(2,4-dimethoxyphenyl)-2-[4'-(2-hydroxy-ethoxy)-phenyl]-1,3-dioxolane Synthesis of 2-(2,4-dimethoxyphenyl)-2-[4'-(2-hydroxy-ethoxy)-phenyl]-1,3-dioxolane as a target substance is synthesized and obtained according to the synthesis of the Reagent A mentioned above, except for using (2,4-dimethoxyphenyl)-[4'-(2-hydroxy-ethoxy)-phenyl]-dimethoxymethane instead of bis-(2,4-dimethoxyphenyl)-dimethoxymethane for the synthesis of Reagent A.

2-(2,4-dimethoxyphenyl)-2-[4'-(2-methacyloxy-ethoxy)-phenyl]-1,3-dioxolane (Reagent B)

Synthesis of 2-(2,4-dimethoxyphenyl)-2-[4'-(2-methacyloxy-ethoxy)-phenyl]-1,3-dioxolane as a target substance is synthesized and obtained according to the synthesis of the Compounder C mentioned above, except for using (2,4-dimethoxyphenyl)-[4'-(2-hydroxy-ethoxy)-phenyl]-dimethoxymethane instead of 2,4-dimethoxy-4'-(2-hydroxy-ethoxy)-benzophenone for the synthesis of Compounder C.

Chem. 5

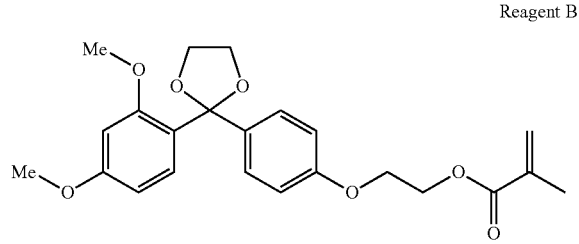

Reagent B

A solution containing 5.0 g of alpha-methacryloyloxy-gamma-butylolactone, 6.03 g of 2-methyladamantane-2-methacrylate, 4.34 g of 3-hydroxyadamantane-1-methacrylate, 0.51 g of dimethyl-2,2'-azobis(2-methylpropionate), and 26.1 g of tetrahydrofuran is prepared. The prepared solution is added dropwise over 4 hours to 20.0 g of tetrahydrofuran placed in flask while stirring and boiling. After the addition of the prepared solution, the mixture is heated to reflux for 2 hours and cooled to room temperature. Addition of the mixture by drops to a mixed liquid containing 160 g of hexane and 18 g of tetrahydrofuran while vigorously stirring precipitates the copolymer. The copolymer is isolated by filtration. Purification of the copolymer is carried out by vacuum drying following two washings by 70 g of hexane, and thereby 8.5 g of white powder of the copolymer is obtained.

Chem. 6

Resin A

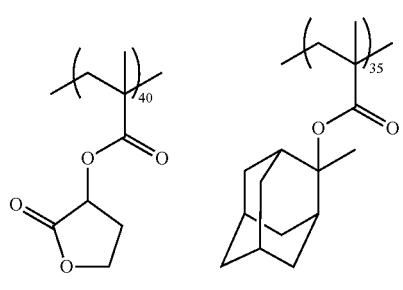

A solution containing 0.82 g of (2,4-dimethoxyphenyl)-[4'-(2-methacryloxy-ethyl)-phenyl]-benzophenone, 3.0 g of alpha-methacryloyloxy-gamma-butylolactone, 2.6 g of 2-methyladamantane-2-methacrylate, 3.1 g of 3-hydroxy-adamantane-1-methacrylate, 0.20 g of butyl mercaptane, 0.51 g of dimethyl-2,2'-azobis(2-methylpropionate) and 11.2 g of tetrahydrofuran is prepared. The prepared solution is added dropwise over 4 hours to 8.0 g of tetrahydrofuran placed in flask while stirring and boiling under nitrogen atmosphere. After the addition of the prepared solution, the mixture is heated to reflux for 2 hours and cooled to room temperature. Addition of the mixture by drops to a mixed liquid containing 110 g of hexane and 11 g of tetrahydrofuran while vigorously stirring precipitates the copolymer. The copolymer is isolated by filtration. Purification of the copolymer is carried out by vacuum drying following two washings by 40 g of hexane, thereby obtaining 7.1 g of white powder of the copolymer (Resin B).

Chem. 7

Resin B

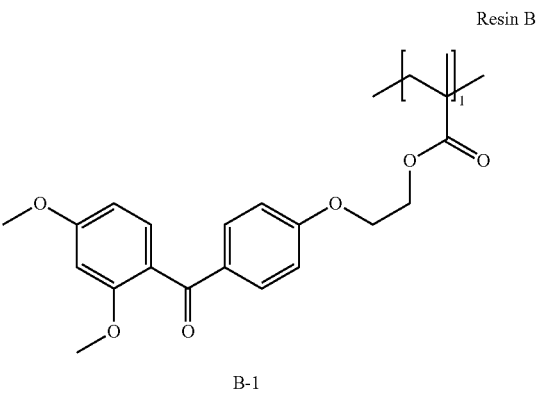

B-1

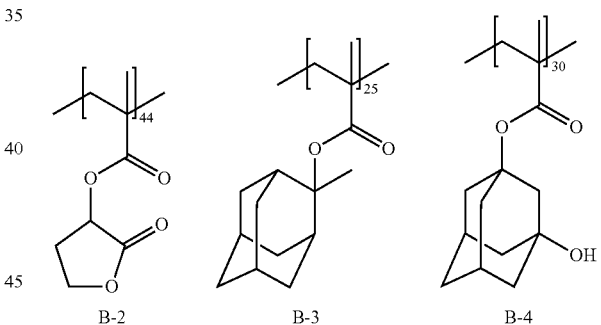

A solution containing 0.92 g of 2-(2,4-dimethoxyphenyl)-2-[4'-(2-methacyloxy-ethoxy)-phenyl]-1,3-dioxolane, 3.0 g of alpha-methacryloyloxy-gamma-butylolactone, 2.6 g of 2-methyladamantane-2-methacrylate, 3.1 g of 3-hydroxy-adamantane-1-methacrylate, 0.20 g of butyl mercaptane, 0.51 g of dimethyl-2,2'-azobis(2-methylpropionate) and 11.2 g of tetrahydrofuran is prepared. The prepared solution is added dropwise over 4 hours to 8.0 g of tetrahydrofuran placed in flask while stirring and boiling under nitrogen atmosphere. After the addition of the prepared solution, the mixture is heated to reflux for 2 hours and cooled to room temperature. Addition of the mixture by drops to a mixed liquid containing 110 g of hexane and 11 g of tetrahydrofuran while vigorously stirring precipitates the copolymer. The copolymer is isolated by filtration. Purification of the copolymer is carried out by vacuum drying following two washings by 40 g of hexane, thereby obtaining 6.8 g of white powder of the copolymer (Resin C).

Chem. 8

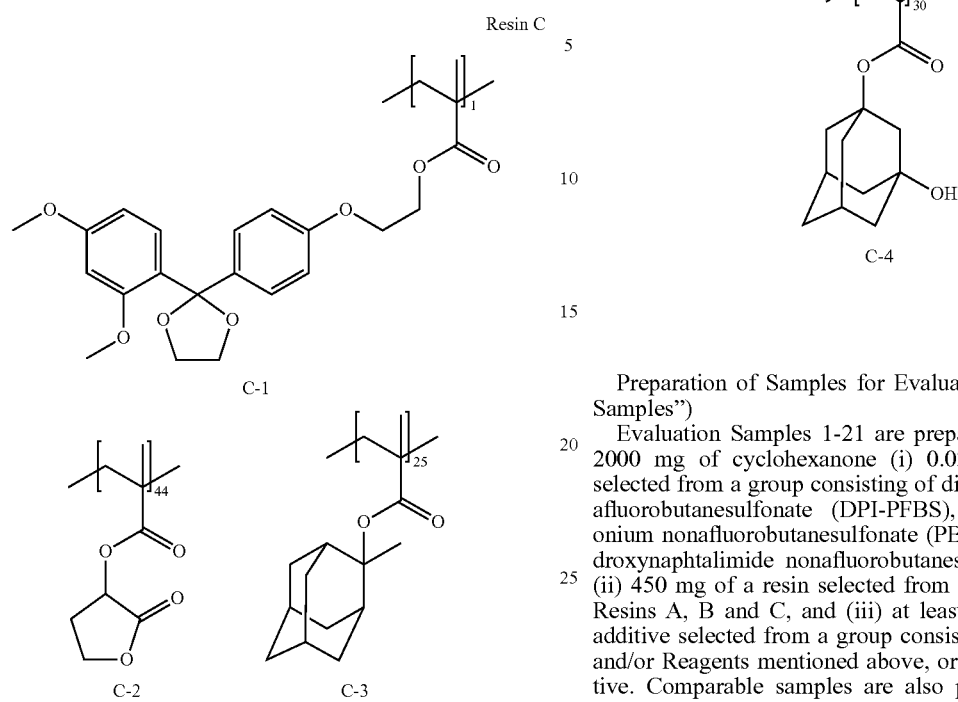

Preparation of Samples for Evaluation (the "Evaluation Samples")

Evaluation Samples 1-21 are prepared by dissolving in 2000 mg of cyclohexanone (i) 0.032 mmol of a PAG selected from a group consisting of diphenyliodonium nonafluorobutanesulfonate (DPI-PFBS), phenyl dibenzothionium nonafluorobutanesulfonate (PBpS-PFBS) and N-hydroxynaphtalimide nonafluorobutanesulfonate (NHNI-Nf), (ii) 450 mg of a resin selected from a group consisting of Resins A, B and C, and (iii) at least 0.017 mmol of one additive selected from a group consisting of Compounders and/or Reagents mentioned above, or (iv) 0 mmol of additive. Comparable samples are also prepared using 0.017 mmol of 2,4-diethylthioxanthen-9-one (DETX) as an additive. Table 1 shows detail of sample compositions.

TABLE 1

| | Resin | PAG | Additive (composition ratio) | Solvent |
| --- | --- | --- | --- | --- |
| Evaluation Sample 1 | Resin A | DPI-PFBS | — | Cyclohexanone |
| Evaluation Sample 2 | | | Compounder A | |
| Evaluation Sample 3 | | | Compounder B | |
| Evaluation Sample 4 | | | Reagent A | |
| Evaluation Sample 5 | | | Reagent A (0.7)    Compounder A (0.3) | |
| Evaluation Sample 6 | | PBpS-PFBS | — | |
| Evaluation Sample 7 | | | Compounder A | |
| Evaluation Sample 8 | | | Compounder B | |
| Evaluation Sample 9 | | | Reagent A (0.7)    Compounder A (0.3) | |
| Evaluation Sample 10 | | NHNI-Nf | — | |
| Evaluation Sample 11 | | | Compounder A | |
| Evaluation Sample 12 | | | Compounder A [0.026 mmol] | |
| Evaluation Sample 13 | | | Compounder A [0.051 mmol] | |
| Evaluation Sample 14 | | | Compounder B | |
| Evaluation Sample 15 | | | Reagent A | |
| Evaluation Sample 16 | Resin B | DPI-PFBS | — | |
| Evaluation Sample 17 | | PBpS-PFBS | — | |
| Evaluation Sample 18 | | NHNI-Nf | — | |
| Evaluation Sample 19 | Resin C | PBpS-PFBS | — | |
| Evaluation Sample 20 | | | Compounder B (0.3) | |
| Evaluation Sample 21 | | NHNI-Nf | — | |
| Comparative sample 1 | Resin A | DPI-PFBS | DETX | |
| Comparative sample 2 | | PBpS-PFBS | DETX | |
| Comparative sample 3 | | NHNI-Nf | DETX | |

Evaluation of Sensitivity

Before applying an Evaluation Sample to an Si wafer, hexamethyldisilazane (HMDS, Tokyo Chemical Industry, Tokyo, JP) is spin-coated at 2000 rpm for 20 seconds on the surface of an Si wafer and baked at 110 degrees Celsius for 1 minute. Then, an Evaluation Sample is spin-coated on the surface Si wafers that have been treated with HMDS at 2000 rpm for 20 seconds to form a coating film. The prebake of the coating film is performed at 110 degrees Celsius for 60 seconds. Then, the coating film of the Evaluation Sample is exposed to an ultraviolet (UV) light, the wavelength of which is 365 nm (i-line) output from a UV exposure system (HMW-661C-3 ORC manufacturing Co. LTD.). After the UV light exposure, a post-exposure-bake (PEB) is carried out at 110 degrees Celsius for 60 seconds. The coating film is developed with NMD-3 (tetra-methyl ammonium hydroxide 2.38%, Tokyo Ohka Kogyo) for 20 seconds at 25 degrees Celsius and rinsed with deionized water for 10 seconds. The thickness of the coating film measured using a film thickness measurement tool is approximately 500 nm. An Evaluation Sample is measured by ultraviolet-visible spectroscopy to evaluate the transmittance of films at 400 nm before UV light irradiation. Thereafter, a sensitivity ($E_0$ sensitivity) is evaluated by measuring the dose size to form a pattern constituted by 100-micrometer lines where the thickness of the coating film is not zero and 100-micrometer spaces where the thickness of the coating film is zero using a UV exposure system, and dose for $E_0$ sensitivity is calculated by means of a measurement of illuminance of UV source by 365 nm illuminometer (USHIO UIT-150, UVD-5365).

Table 2 shows the dose sizes corresponding to $E_0$ sensitivities measured for the Evaluation Samples 1 to 21. Formation of acid by an irradiation by i-line UV exposure is not observed for Evaluation Samples 1, 6 and 19. A tiny amount of acid is generated for Evaluation Sample 4. The $E_0$ sensitivities are high for Evaluation Samples containing Compounder A, which has higher electron-donating ability than Compounder B.

Resin B shows higher sensitivity than Compounder B, although the electron-donating ability of B-1 moiety included in Resin B acting as a photosensitizer is similar to that of Compounder B. An incorporation of B-1 moieties acting as photosensitizers into polymer enables homogeneous dispersion of the photosensitizers, which improves acid generation efficiency.

Each of Evaluation Samples 5, 9 and 20 contains a photosensitizer and reagent that is protected by a protecting group such as dialkoxy acetal and to form a corresponding photosensitizer through reaction with acid. Such reagents and photosensitizers corresponding to such reagents have two pi-electron systems. In other words, such reagents and photosensitizers are two aromatic groups. An electronic interaction between the two pi-electron systems of such reagent is weaker than that of a corresponding photosensitizer. The two pi-electron systems of such photosensitizer interact mutually through pi electrons or unshared electron pair of carbonyl group of such photosensitizer. Due to such an electronic interaction in the photosensitizer, the photosensitizer can absorb a long-wavelength light.

The conjugation length of such a reagent is shorter than that of a corresponding photosensitizer. In the photosensitizer, conjugation length is longer because of the electronic interaction of the two pi-electron systems through pi electrons or unshared electron pair of a carbonyl group.

Addition of the reagent provides a composition containing the reagent and PAG having preservation stability. A film formed from such a composition has long-term reliability because the reagent has difficulty absorbing long-wavelength UV light due to a weaker electronic interaction between the two pi-electron systems. Such composition is especially useful for constituent material for film (e.g., insulating film or planarizing film of a display device), because suppressing the formation of acid can be achieved during normal operation of the display device.

TABLE 2

|  | Dose for $E_0$ Dose at 365 nm [mJ/cm$^2$] | Transmittance at 400 nm |
|---|---|---|
| Evaluation Sample 1 | >1000 | 99.9 |
| Evaluation Sample 2 | 160 | 99.7 |
| Evaluation Sample 3 | 190 | 99.8 |
| Evaluation Sample 4 | 950 | 99.9 |
| Evaluation Sample 5 | 175 | 99.9 |
| Evaluation Sample 6 | >1000 | 99.8 |
| Evaluation Sample 7 | 190 | 99.7 |
| Evaluation Sample 8 | 225 | 99.8 |
| Evaluation Sample 9 | 210 | 99.8 |
| Evaluation Sample 10 | 210 | 99.7 |
| Evaluation Sample 11 | 40 | 99.7 |
| Evaluation Sample 12 | 30 | 99.7 |
| Evaluation Sample 13 | 20 | 99.6 |
| Evaluation Sample 14 | 50 | 99.7 |
| Evaluation Sample 15 | 45 | 99.8 |
| Evaluation Sample 16 | 140 | 99.8 |
| Evaluation Sample 17 | 170 | 99.7 |
| Evaluation Sample 18 | 40 | 99.7 |
| Evaluation Sample 19 | >1000 | 99.7 |
| Evaluation Sample 20 | 170 | 99.7 |
| Evaluation Sample 21 | 45 | 99.7 |
| Comparative sample 1 | 125 | 87.6 |
| Comparative sample 2 | 130 | 87.6 |
| Comparative sample 3 | 30 | 87.3 |

Alkoxy groups and aryloxy groups are electron-donating groups on aromatic group that can enhance the photosensitizing function of ketones. Besides a methoxy group, such include alkoxy groups having more than one carbon atom, such as ethoxy, n-propoxy group, i-propoxy, n-butyl, sec-butyl and t-butyl groups. Aryloxy groups such as phenoxy and naphthoxy groups are also available. Aryloxy groups containing at least one hetero atom such as pylidyloxy and thiophenyloxy groups can be selected as electron-donating groups.

In addition to alkoxy and aryloxy groups, hydroxy, amino, alkylthio and arylthio groups can be introduced into an aromatic group such as electron-donating groups.

It is preferable that at least one of such electron-donating groups including methoxy group is at the para-position or an ortho-position of the aromatic group with regard to the carbonyl group. In other words, it is preferable that such electron-donating group is positioned such that compounder can express the electron-donating nature.

Each of Compounders D, E, F, and derivatives thereof is also preferably used as a photosensitizer. Each of the Compounders has electron-donating character that can function as a photosensitizer by UV light exposure because such compounder has at least one atom having an unshared electron pair. An electron of an unshared electron pair can be transferred to another moiety intramolecularly or another molecule intermolecularly.

Chem. 9

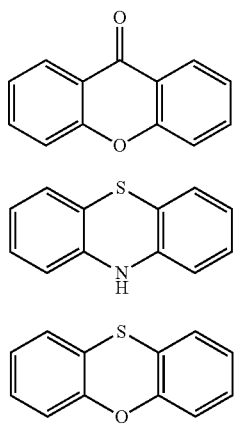

Compounder D

Compounder E

Compounder F

Groups containing at least two chalcogen atomes, such as acetal, 1,3-dioxolane, thioacetal and 1,3-dithiolane, can be used as protecting groups for a carbonyl group.

FIG. 1 shows absorption spectra of Compounder A, Compounder B, thioxanthone and dibutoxyanthracene in a solution (top) and of Compounder A, Compounder B, thioxanthone and dibutoxyanthracene in a film (bottom). Compounder A and Compounder B exhibit little absorption at wavelengths longer than 400 nm. Therefore, Compounder A and Compounder B are especially suitable for photosensitizers enhancing generation of acid from PAG contained in a photoresist applicable to fabrication of an interlayer insulating film of a display device such as a liquid crystal device and an organic electroluminescent device. Compounder A or Compounder B is also useful as a constituent of material forming an interlayer insulating film of such a display device because Compounder A and Compounder B can hardly absorb light, the wavelength of which is longer than 400 nm, which is desired to pass through the interlayer insulating film. Visible light usually passes through interlayer insulating films of display devices for performing the display. If a substance that can act as a photosensitizer or PAG by absorbing a visible light remains in an interlayer insulating film, acid is generated even during normal operations and deteriorates the display device.

Typically, the molar absorption coefficient at 400 nm of a photosensitizer relating to an aspect of this disclosure in a solution is equal to or lower than 400. It is preferred that the molar absorption coefficient is equal to or lower than 200. More preferably, the molar absorption coefficient is equal to or lower than 100. The molar absorption coefficients of Compounder A and Compounder B are equal to or lower than 50.

A typical ratio of absorbance at 365 nm ("$Ab_{365}$") to absorbance at 400 nm ("$Ab_{400}$") in a solution is equal to or greater than 10. A preferable $Ab_{365}/Ab_{400}$ in a solution is equal to or greater than 20. A more preferable $Ab_{365}/Ab_{400}$ in a solution is equal to or greater than 50. A preferable $Ab_{365}/Ab_{400}$ in a film is equal to or greater than 50. A more preferable $Ab_{365}/Ab_{400}$ in a film is equal to or greater than 100.

Figure 2:
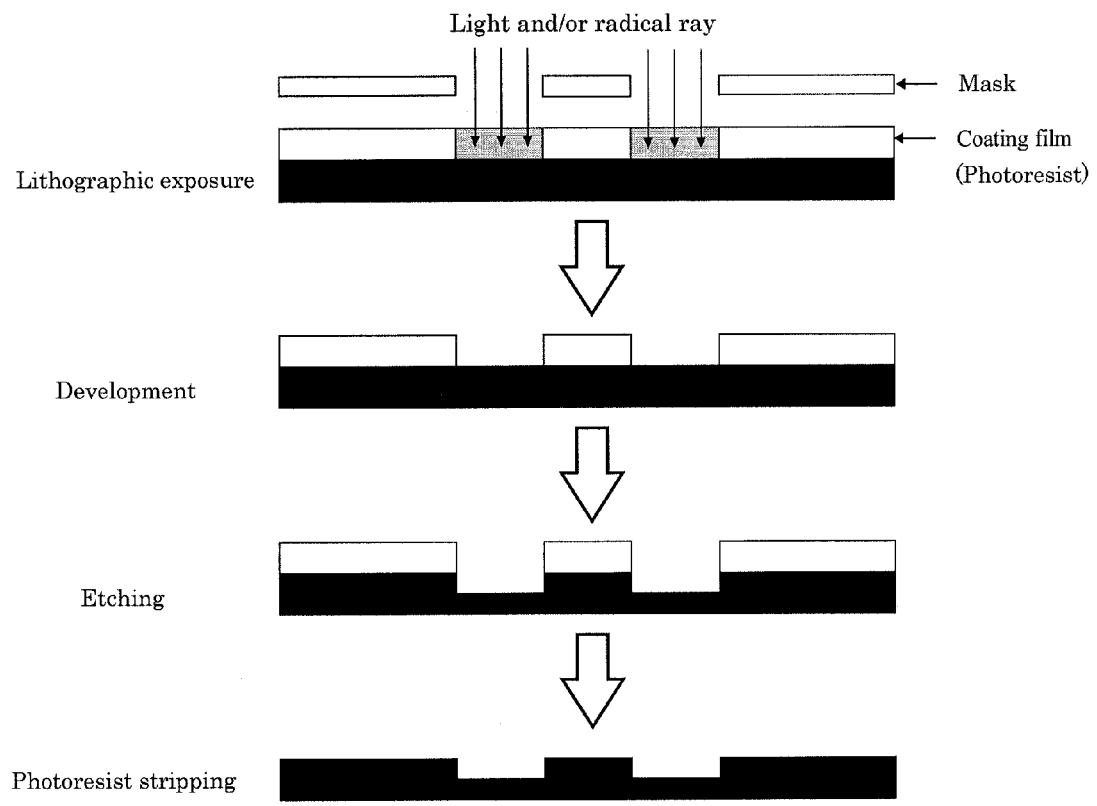
FIG. 2 shows fabrication processes of a device such as an integrated circuit (IC) using a photoresist relating to an aspect of this disclosure.

FIG. 2 shows fabrication processes of a device such as an integrated circuit (IC) using a photoresist including Reagent A and a small amount of Compounder A obtained by the processes by the above procedures.

A silicon wafer is provided. The surface of a silicon wafer is oxidized by heating the silicon wafer in the presence of oxygen gas.

A solution of a chemically amplified resist (CAR) composition including Reagent A, resin, and PAG is applied to the surface of an Si wafer by spin coating to form a coating film. The coating film is prebaked.

An irradiation of the coating film with a light, the wavelength of which is equal to or longer than 220 nm, is carried out through a mask after prebake of the Si wafer. A typical light source for the irradiation of the coating film is i-line or g-line. Initially, the PAG generates a small quantity of acid by absorbing the light directly. An encounter of reagent A with the small quantity of acid yields a deprotection reaction of Reagent A to form a photosensitizer in situ. The deprotection reaction of resin A is induced by acid generated by photoreaction of the photoacid generator and assistance by the photosensitizer formed in situ.

The conjugation length of the photosensitizer is longer than the conjugation length of the reagent. The reagent has at least two pi-electron systems. By formation of a multiple bond through the deprotection reaction of the reagent, the electronic interaction between the at least two pi-electron systems in the photosensitizer is stronger than the electronic interaction between the at least two pi-electron systems in the reagent.

The coating film and the silicon wafer are exposed to the light. After that, the remaining film is removed.

An electronic device such as an integrated circuit is fabricated utilizing the processes shown in FIG. 2. The deterioration of the device due to the irradiation with a light is suppressed compared to existing photoresists, since times for irradiation of the coating film can be shortened.

FIGS. 3A through 3I show fabrication processes for active matrix-type organic electroluminescent devices.

Figure 3A:
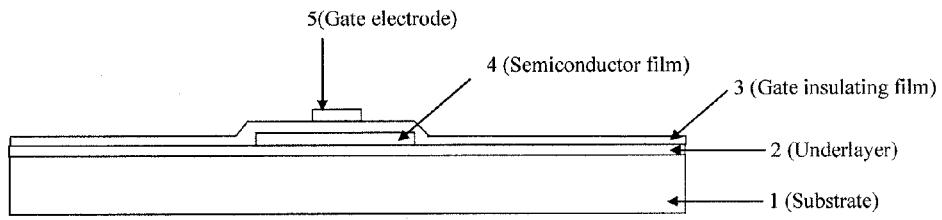
FIGS. 3A-3I show fabrication processes of a display device such as an organic electroluminescent device (OLED) using a photoresist relating to an aspect of this disclosure.

FIG. 3A: Underlayer 2 is formed on a substrate 1 such as a glass substrate, a quartz substrate and a plastic substrate. Semiconductor film 4, which is formed by patterning, is formed on underlayer 2. Typically, semiconductor film 4 is made of low-temperature polysilicon. Amorphous silicon or metal oxide can also be used as material for semiconductor film 4. Gate insulating film 3 is formed such that gate insulating film 3 covers semiconductor film 4. Gate electrode 5 is formed over gate insulating film 3 such that gate electrode 5 and semiconductor film 4 face each other across gate insulating film 3.

Figure 3B:
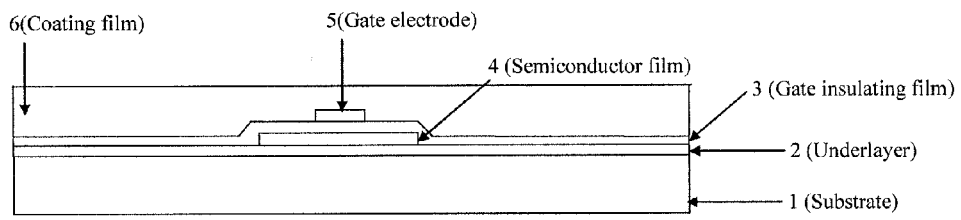

FIG. 3B: Coating film 6 is disposed by spin-coating of a composition containing Resin D such that coating film 6 covers gate electrode 5 and gate insulating film 3. D-1 moiety of Resin D is to react a chemical species such as acid generated from photoacid generating moiety D-5 to form a corresponding deprotected moiety that can act as a photosensitizing moiety. In other words, such photosensitizing moiety formed in situ can interact with a moiety through electron exchange. According to circumstances, compounder that can act as photosensitizer on its own, such as Compounder A and Compounder B, can be contained in the composition. Resin D may further include a moiety acting as a photosensitizer on its own like B-1 in addition to D1, D2, D3, D4, D5 and D6.

Chem. 10

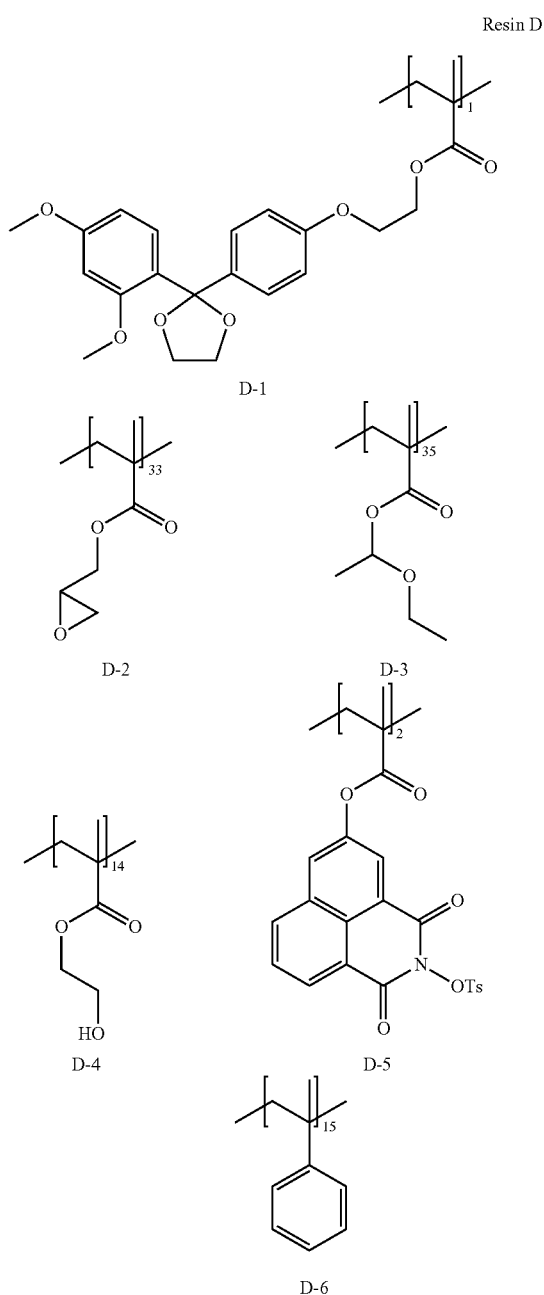

Figure 3C:
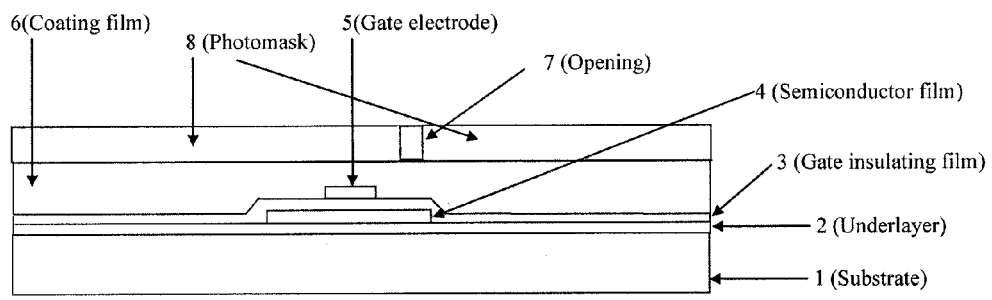

FIG. 3C: Coating film 6 is irradiated with a light, the wavelength of which is 365 nm, through photomask 8 after coating film 6 is subjected to prebake treatment. Only a portion of coating film 6 is exposed to a light passing through opening 7.

Figure 3D:
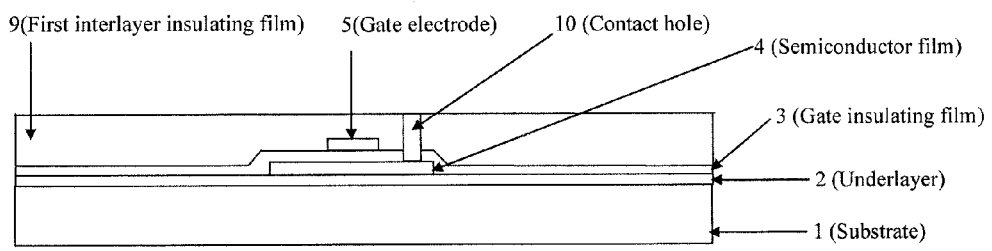

FIG. 3D: The exposed portion of coating film 6 by the light is removed by development to form contact hole 10. Coating film 6 is converted into first interlayer insulating film 9 by a heat treatment carried out at a temperature higher than 150 degrees centigrade following formation of contact hole 10.

Figure 3E:
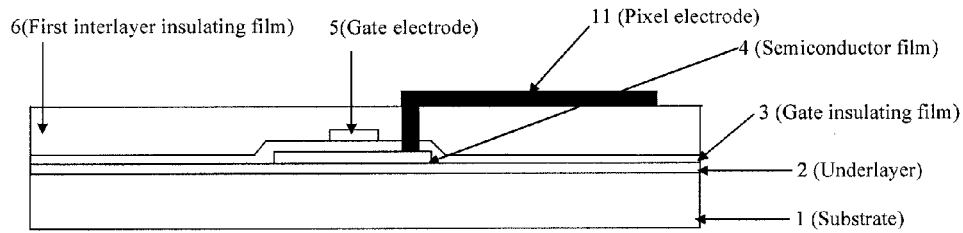

FIG. 3E: Pixel electrode 11, which is electrically connected to semiconductor film 4, is formed. Typically, pixel electrode 11 is made of Indium Tin Oxide (ITO) or magnesium-silver alloy.

Figure 3F:
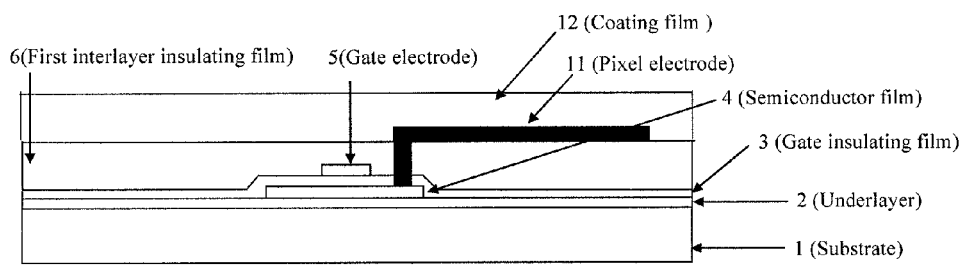

FIG. 3F: Coating film 12 is disposed by a spin-coating process such that coating film 12 covers pixel electrode 11 and first interlayer insulating film 9.

Figure 3G:
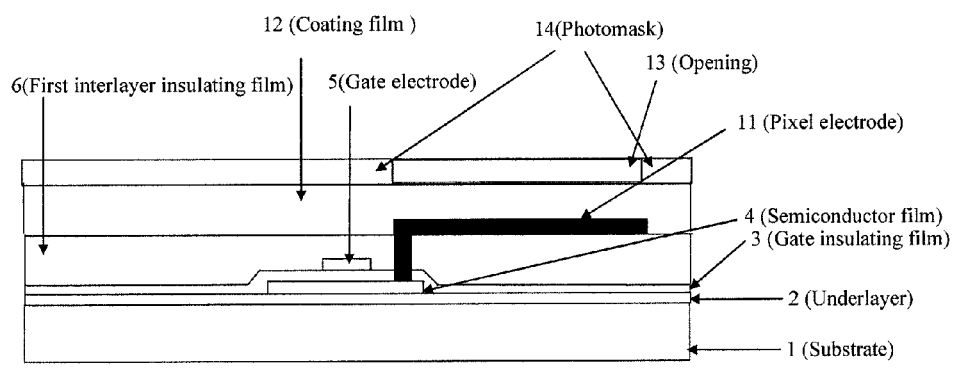

FIG. 3G: Coating film 12 is irradiated with a light, the wavelength of which is 365 nm, through photomask 14 after coating film 12 is subjected to prebake treatment. Only a portion of coating film 12 is exposed to a light passing through opening 13.

Figure 3H:
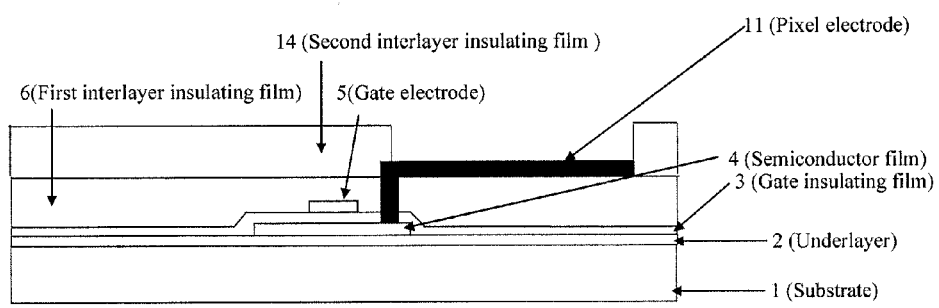

FIG. 3H: The exposed portion of coating film 12 by the light is removed by development. Coating film 12 is converted into second interlayer insulating film 14 by a heat treatment carried out at a temperature higher than 150 degrees centigrade following removal of the exposed portion of coating film 12.

Figure 3I:
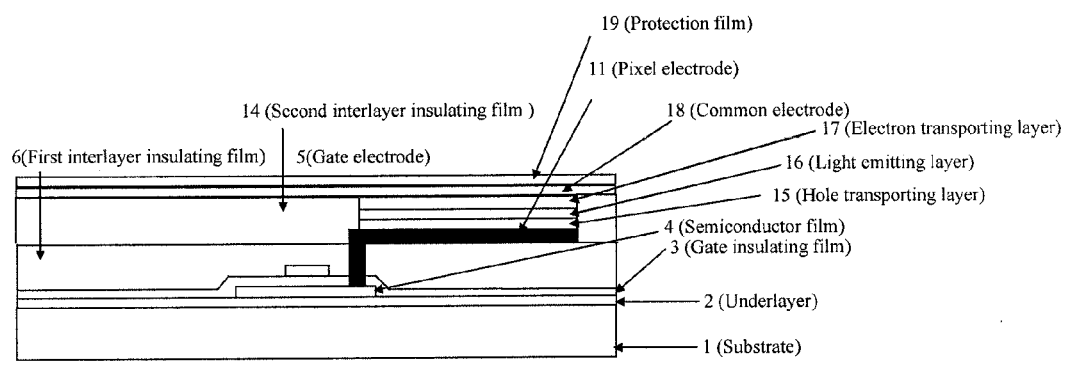

FIG. 3I: Hole transport layer 15, light-emitting layer 16 and electron transporting layer 17 are formed by vacuum vapor deposition via mask in this order. Common electrode 18 is formed over electron transporting layer 17 and second interlayer insulating film 14. Protection film 19 is formed over common electrode 18.

The invention claimed is:

1. A composition, comprising:
   a compounder;
   a polymer containing an acid-dissociable substituent; and
   a precursor,
   wherein the compounder:
      has a diaryl ketone skeleton with at least one electron-donating group on at least one aromatic group of the diaryl ketone skeleton;
      absorbs a light, the wavelength of which is longer than 220 nm;
      is capable of sensitizing the precursor to generate a chemical species from the precursor; and
      wherein the electron-donating group is selected from the group consisting of an alkoxy group, aryloxy group, aryloxy group containing at least hereto atom, hydroxyl group, amino group, alkylthio group, and arylthio group.

2. The composition of claim 1, wherein the compounder has a molar absorption coefficient of the compounder at 400 nm when measured in a solution is equal to or lower than 200.

3. The composition according to claim 1, wherein the precursor is a photoacid generator (PAG).

4. The composition according to claim 1, further comprising:
   a compound capable of reacting with the chemical species.

5. The composition of claim 1, wherein the compounder has three or more electron-donating groups.

6. A polymer, comprising:
   a first moiety capable of acting as a photosensitizing moiety; and
   a second moiety that is to react with a chemical species and contains an acid-dissociable substituent,
      wherein the first moiety is a group connected with a compounder having a diaryl ketone skeleton with at least one electron-donating group on at least one aromatic group of the diaryl ketone skeleton;
      absorbs a light, the wavelength of which is longer than 220 nm; and
      is capable of sensitizing the precursor to generate a chemical species from the precursor, and
      wherein the electron-donating group is selected from the group consisting of an alkoxy group, aryloxy group, aryloxy group containing at least hereto atom, hydroxyl group, amino group, alkylthio group, and arylthio group.

7. The polymer according to claim 6, further comprising: a third moiety that is to generate the chemical species.

8. The polymer of claim 6, wherein the compounder has three or more electron-donating groups.

9. A method for manufacturing a device, wherein the method comprises:
applying a solution of the composition of claim 1 to a member such that a coating film including the composition is formed on the member; and
irradiating the coating film with at least one of an electromagnetic ray and a particle ray, such that a first portion of the coating film is exposed to the at least one of the electromagnetic ray and the particle ray while a second portion of the coating film is not exposed to the at least one of the electromagnetic ray and the particle ray; and
removing the first portion.

10. The method according to claim 9, wherein
the device comprises an interlayer insulating film, and
the composition is used for formation of the interlayer insulating film.

11. The method according to claim 9, further comprising:
etching the member such that a third portion of the member on which the first portion has been present is etched.

12. The method according to claim 9, wherein the electromagnetic ray is a light with a wavelength ranging between 350 nm and 400 nm.

13. The method according to claim 9, wherein an electromagnetic ray is used to irradiate the coating film with a light having a wavelength ranging between 310 nm and 400 nm.

14. The method according to claim 9, wherein the compounder has three or more electron-donating groups.

* * * * *